(12) United States Patent
Demmer et al.

(10) Patent No.: US 9,452,292 B2
(45) Date of Patent: Sep. 27, 2016

(54) METHOD AND APPARATUS FOR DETECTING LOSS OF CAPTURE

(71) Applicant: Medtronic, Inc., Minneapolis, MN (US)

(72) Inventors: Wade M Demmer, Coon Rapids, MN (US); Douglas A Peterson, Apple Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 70 days.

(21) Appl. No.: 14/261,776

(22) Filed: Apr. 25, 2014

(65) Prior Publication Data

US 2015/0306401 A1  Oct. 29, 2015

(51) Int. Cl.
| | |
|---|---|
| *A61N 1/00* | (2006.01) |
| *A61N 1/37* | (2006.01) |
| *A61B 5/0452* | (2006.01) |
| *A61N 1/375* | (2006.01) |
| *A61N 1/362* | (2006.01) |

(Continued)

(52) U.S. Cl.
CPC ......... *A61N 1/3702* (2013.01); *A61B 5/04525* (2013.01); *A61N 1/371* (2013.01); *A61N 1/3712* (2013.01); *A61N 1/3756* (2013.01); *A61B 2017/00203* (2013.01); *A61N 1/365* (2013.01); *A61N 1/3622* (2013.01); *A61N 1/3624* (2013.01)

(58) Field of Classification Search
CPC .................................................. A61N 1/3702
USPC ............................ 600/519; 607/2, 22, 27, 30
See application file for complete search history.

(56) References Cited

U.S. PATENT DOCUMENTS

| | | |
|---|---|---|
| 761,162 A | 5/1904 | Gold |
| 4,374,382 A | 2/1983 | Markowitz |
| 4,476,868 A | 10/1984 | Thompson |

(Continued)

FOREIGN PATENT DOCUMENTS

| | | |
|---|---|---|
| CN | 1838076 A | 9/2006 |
| EP | 1 116 495 A2 | 7/2001 |

(Continued)

OTHER PUBLICATIONS (PCT/US2015/062137) Invitation to Pay Additional fees and, where applicable, protest fee, mailed Mar. 1, 2016, 8 pages.

(Continued)

*Primary Examiner* — Theodore Stigell
*Assistant Examiner* — Nadia A Mahmood
(74) *Attorney, Agent, or Firm* — Evans M. Mburu

(57) ABSTRACT

A method and apparatus for determining stability of a patient's intrinsic rhythm in a cardiac pacing device. Cardiac pacing pulses are delivering to a chamber of a patient's heart by the pacing device at a first pulse amplitude. The device measures a first series of intervals between successive sensed and paced events. The device then determines whether the first measured series of intervals meets a stability criterion. Responsive to the first measured series of intervals failing to meet the stability criterion, the device determines whether the first measured series of intervals includes an interval between a delivered pacing pulse and a sensed event that is less than a defined duration. Responsive to the interval between a delivered pacing pulse and a sensed event being less than the defined duration, the device delivers cardiac pacing pulses to the chamber of a patient's heart at a second pulse amplitude and measures a second series of intervals between successive sensed and paced events and determines whether the second measured series of intervals meets the stability criterion.

27 Claims, 8 Drawing Sheets

(51) Int. Cl.
*A61N 1/365* (2006.01)
*A61B 17/00* (2006.01)

(56) References Cited

U.S. PATENT DOCUMENTS

| | | | |
|---|---|---|---|
| 4,485,813 | A | 12/1984 | Anderson et al. |
| 5,052,388 | A | 10/1991 | Sivula et al. |
| 5,074,302 | A | 12/1991 | Poore et al. |
| 5,117,824 | A | 6/1992 | Keimel et al. |
| 5,154,170 | A | 10/1992 | Bennett et al. |
| 5,165,404 | A | 11/1992 | Andersson et al. |
| 5,165,405 | A | 11/1992 | Elkwall |
| 5,172,690 | A | 12/1992 | Nappholz et al. |
| 5,190,034 | A | 3/1993 | Sholder |
| 5,222,493 | A * | 6/1993 | Sholder ............ A61N 1/371 607/27 |
| 5,226,413 | A | 7/1993 | Bennett et al. |
| 5,231,986 | A | 8/1993 | Bennett |
| 5,285,780 | A | 2/1994 | Tsuji et al. |
| 5,304,208 | A | 4/1994 | Inguaggiato et al. |
| 5,312,454 | A | 5/1994 | Roline et al. |
| 5,320,643 | A | 6/1994 | Roline et al. |
| 5,324,310 | A | 6/1994 | Greeninger et al. |
| 5,345,362 | A | 9/1994 | Winkler |
| 5,354,317 | A | 10/1994 | Alt |
| 5,423,867 | A | 6/1995 | Poore et al. |
| 5,447,525 | A | 9/1995 | Powell et al. |
| 5,496,351 | A | 3/1996 | Plicchi et al. |
| 5,507,782 | A | 4/1996 | Kieval et al. |
| 5,507,785 | A | 4/1996 | Deno |
| 5,562,711 | A | 10/1996 | Yerich et al. |
| 5,593,431 | A | 1/1997 | Sheldon |
| 5,601,615 | A | 2/1997 | Markowitz et al. |
| 5,609,612 | A | 3/1997 | Plicchi et al. |
| 5,628,777 | A | 5/1997 | Moberg et al. |
| 5,683,432 | A | 11/1997 | Goedeke et al. |
| 5,693,075 | A | 12/1997 | Plicchi et al. |
| 5,720,769 | A | 2/1998 | van Oort et al. |
| 5,755,740 | A | 5/1998 | Nappholz |
| 5,766,230 | A | 6/1998 | Routh et al. |
| 5,782,889 | A | 7/1998 | Hognelid et al. |
| 5,944,745 | A | 8/1999 | Rueter |
| 5,954,755 | A | 9/1999 | Casavant |
| 6,044,297 | A | 3/2000 | Sheldon et al. |
| 6,389,316 | B1 | 5/2002 | Bornzin et al. |
| 6,449,508 | B1 | 9/2002 | Sheldon et al. |
| 6,553,259 | B2 | 4/2003 | Mouchawar et al. |
| 6,772,005 | B2 | 8/2004 | Casavant et al. |
| 6,819,955 | B2 | 11/2004 | Levine |
| 6,950,704 | B1 | 9/2005 | Bradley |
| 7,031,772 | B2 | 4/2006 | Condie et al. |
| 7,076,283 | B2 | 7/2006 | Cho et al. |
| 7,130,690 | B2 | 10/2006 | Rueter et al. |
| 7,280,868 | B2 | 10/2007 | Rueter et al. |
| 7,400,924 | B2 | 7/2008 | Rueter |
| 7,457,666 | B2 | 11/2008 | Bohn et al. |
| 7,532,930 | B2 | 5/2009 | Schermeier et al. |
| 7,761,162 | B2 | 7/2010 | Dong et al. |
| 7,778,696 | B2 | 8/2010 | Sathaye |
| 7,783,355 | B2 | 8/2010 | Rueter |
| 7,818,059 | B2 | 10/2010 | Rueter et al. |
| 7,831,303 | B2 | 11/2010 | Rueter et al. |
| 8,280,509 | B2 | 10/2012 | Sathaye |
| 8,433,409 | B2 | 4/2013 | Johnson et al. |
| 8,532,785 | B1 | 9/2013 | Crutchfield et al. |
| 8,541,131 | B2 | 9/2013 | Lund et al. |
| 2002/0183798 | A1 | 12/2002 | Vonk |
| 2003/0069611 | A1 | 4/2003 | Levine |
| 2003/0078624 | A1 | 4/2003 | Carlson et al. |
| 2003/0078627 | A1 | 4/2003 | Casavant et al. |
| 2003/0083700 | A1 | 5/2003 | Hill |
| 2003/0083712 | A1 | 5/2003 | Rueter et al. |
| 2003/0195579 | A1 | 10/2003 | Bradley et al. |
| 2003/0204214 | A1 | 10/2003 | Ferek-Patric |
| 2004/0030358 | A1 | 2/2004 | Rueter et al. |
| 2004/0088019 | A1 | 5/2004 | Rueter et al. |
| 2004/0260352 | A1 | 12/2004 | Rueter et al. |
| 2005/0015985 | A1 | 1/2005 | Dvoskin |
| 2005/0021095 | A1 | 1/2005 | Rueter et al. |
| 2005/0159785 | A1 | 7/2005 | Rueter |
| 2005/0222630 | A1 | 10/2005 | Schermeier et al. |
| 2006/0155338 | A1 | 7/2006 | Mongeon et al. |
| 2006/0241710 | A1 | 10/2006 | Rueter |
| 2006/0247705 | A1 | 11/2006 | Rueter et al. |
| 2007/0115277 | A1 | 5/2007 | Wang et al. |
| 2010/0010380 | A1 | 1/2010 | Panken et al. |
| 2010/0010583 | A1 | 1/2010 | Panken et al. |
| 2011/0012759 | A1 | 1/2011 | Yin |
| 2011/0029034 | A1 | 2/2011 | Fischer et al. |
| 2011/0152963 | A1 | 6/2011 | Stahmann et al. |
| 2012/0065524 | A1 | 3/2012 | Morren et al. |
| 2012/0109259 | A1 | 5/2012 | Bond et al. |
| 2012/0172892 | A1 | 7/2012 | Grubac et al. |
| 2012/0245476 | A1 | 9/2012 | Skerl et al. |
| 2013/0035748 | A1 | 2/2013 | Bonner et al. |
| 2013/0079861 | A1 | 3/2013 | Reinert et al. |
| 2013/0090702 | A1 | 4/2013 | Mongeon et al. |
| 2013/0116602 | A1 | 5/2013 | Van Den Heuvel et al. |
| 2013/0150911 | A1 | 6/2013 | Perschbacher et al. |
| 2013/0211205 | A1 | 8/2013 | Havel et al. |
| 2013/0289652 | A1 | 10/2013 | Skelton et al. |
| 2015/0217119 | A1 | 8/2015 | Nikolski et al. |
| 2015/0238769 | A1 | 8/2015 | Demmer et al. |

FOREIGN PATENT DOCUMENTS

| | | |
|---|---|---|
| EP | 1116495 A2 | 7/2001 |
| EP | 2239007 A1 | 10/2010 |

OTHER PUBLICATIONS (PCT/US2015/062137) Invitation to Pay Additional Fees and, where applicable, protest fee.
U.S. Appl. No. 14/174,514, filed Feb. 6, 2014.
(PCT/US2015/013729) PCT Notification of Transmittal of the International Search Report and the Written Opinion of the International Searching Authority.
(PCT/US2014/070598) PCT Notification of Transmittal of the International Search Report and the Written Opinion of the International Searching Authority.
Demmer, et al., "Method and Apparatus for Detecting Loss of Capture", U.S. Appl. No. 14/261,776, filed Apr. 25, 2014, 44 pages.
(PCT/US2014/067337) PCT Notification of Transmittal of the International Search Report and the Nritten Opinion of the International Searching Authority.
U.S. Appl. No. 14/552,758, filed Nov. 25, 2014.
(PCT/US2015/027055) PCT Notification of Transmittal of the International Search Report and the Written Opinion of the International Searching Authority, mailed Sep. 30, 2015, 9 pages.
Telectronics Meta 1254 DDDr Physician Manual, Chapter 8 (46 pages).
Telectronics Meta 1254 DDDr Physician Manual (55 pages).

* cited by examiner

METHOD AND APPARATUS FOR DETECTING LOSS OF CAPTURE

CROSS-REFERENCE TO RELATED APPLICATIONS

This application is related to U.S. Provisional Application No. 61/912,189, filed on Feb. 24, 2014, now lapsed and to U.S. patent application Ser. No. 14/248,646, filed Apr. 9, 2014, now lapsed. The disclosures of the above applications are incorporated herein by reference in their entireties.

TECHNICAL FIELD

This disclosure relates to implantable medical devices and, more particularly, to miniaturized implantable medical devices.

BACKGROUND

A variety of medical devices for delivering a therapy and/or monitoring a physiological condition have been used clinically or proposed for clinical use in patients. Examples include medical devices that deliver therapy to and/or monitor conditions associated with the heart, muscle, nerve, brain, stomach or other organs or tissue. Some therapies include the delivery of electrical signals, e.g., stimulation, to such organs or tissues. Some medical devices may employ one or more elongated electrical leads carrying electrodes for the delivery of therapeutic electrical signals to such organs or tissues, electrodes for sensing intrinsic electrical signals within the patient, which may be generated by such organs or tissue, and/or other sensors for sensing physiological parameters of a patient. Some medical devices may be "leadless" and include one or more electrodes on an outer housing of the medical device to deliver therapeutic electrical signals to organs or tissues and/or sense intrinsic electrical signals or physiological parameters of a patient.

Medical leads may be configured to allow electrodes or other sensors to be positioned at desired locations for delivery of therapeutic electrical signals or sensing. For example, electrodes or sensors may be carried at a distal portion of a lead. A proximal portion of the lead may be coupled to a medical device housing, which may contain circuitry such as signal generation and/or sensing circuitry. In some cases, the medical leads and the medical device housing are implantable within the patient, while in other cases percutaneous leads may be implanted and connected to a medical device housing outside of the patient. Medical devices with a housing configured for implantation within the patient may be referred to as implantable medical devices. Leadless medical devices are typically implantable medical devices positioned within or adjacent to organs or tissues within a patient for delivery of therapeutic electrical signals or sensing. In some example, leadless implantable medical devices may be anchored to a wall of an organ or to tissue via a fixation mechanism.

Implantable cardiac pacemakers or cardioverter-defibrillators, for example, provide therapeutic electrical signals to the heart, e.g., via electrodes carried by one or more medical leads or via electrodes on an outer housing of a leadless implantable medical device. The therapeutic electrical signals may include pulses for pacing, or shocks for cardioversion or defibrillation. In some cases, a medical device may sense intrinsic depolarizations of the heart, and control delivery of therapeutic signals to the heart based on the sensed depolarizations. Upon detection of an abnormal rhythm, such as bradycardia, tachycardia or fibrillation, an appropriate therapeutic electrical signal or signals may be delivered to restore or maintain a more normal rhythm. For example, in some cases, an implantable medical device may deliver pacing stimulation to the heart of the patient upon detecting tachycardia or bradycardia, and deliver cardioversion or defibrillation shocks to the heart upon detecting fibrillation.

In general, implantable medical devices require a small housing form factor to enable an unobtrusive implantation within a patient. In the case of leadless implantable medical devices, the housing form factor must be extremely small to enable implantation within or adjacent to organs or tissue. For example, a leadless pacemaker may be implanted directly into a ventricle of the heart. Battery usage is always a concern when designing implantable medical devices, but this concern is increased for small form factor devices that can only accommodate a small battery canister.

Currently, many implantable devices attempt to minimize battery drain by means of capture management testing, as described in U.S. Pat. Nos. 5,601,615, 5,766,230, 6,553,259, 7,280,868, 7,457,666, and 7,761,162, incorporated herein by reference in their entireties. Such tests determine the pacing pulse threshold parameters (typically voltage and pulse width) necessary to capture the chamber of the heart being paced. These tests are also referred to as threshold tests.

The devices typically thereafter set the actual parameters to a higher energy level than the determined threshold parameters, typically to a higher voltage. By this mechanism, the devices provide a safety margin which decreases the likelihood that changes in the underlying condition of the patient's heart will result in a loss of capture. Such capture management tests may be performed according to defined pre-programmed schedules or in response to events indicating that capture is no longer reliably occurring.

Correspondingly, many devices include the associated capability to detect loss of capture. Such devices are disclosed in the patents cited above. Actual loss of capture may be detected on a beat to beat basis or by changes in detected cardiac rhythm. Detected loss of capture may trigger the performance of a threshold test, as discussed in the above-cited patents. The result will typically be a resetting of pacing parameters to parameters that provide the defined safety margin or by resetting to the maximum energy level deliverable by the device, whichever is less.

Many current devices employ capture management operations such as threshold measurement tests and safety margin checks as described in the above cited patents. In many cases, the presence of a stable intrinsic cardiac rhythm is a prerequisite to successful testing. Emergence of the patient's underlying rhythm may in some cases cause such capture management tests to fail. As a prerequisite to performing a threshold test or safety margin check, it is therefore desirable to first determine that the patient's underlying heart rhythm is stable. One mechanism for assessing stability for this purpose is set forth in the above-cited '868 patent. The present invention is directed to an improvement to such a stability check.

SUMMARY

The details of one or more aspects of the disclosure are set forth in the accompanying drawings and the description below. Other features, objects, and advantages of the disclosure will be apparent from the description and drawings, and from the claims.

In order to develop further miniaturized pacing devices such as leadless pacemakers, methods of further reducing unneeded current drain are highly desirable. In many contemporary devices, a substantial amount of battery capacity is spent by pacing at large voltage margin (safety margin) over the pacing threshold. However, reducing the safety margin correspondingly brings an increased risk of loss of capture. One approach to addressing this issue is set forth in the above-cited '646 application, wherein the device monitors for evidence that the patient's underlying rhythm is occurring despite the presence of pacing. Because this situation is indicative of a loss of pacing capture, it can be used to identify potential loss of capture and start a new capture management test. This mechanism is substantially less complicated than detection of loss of capture on a beat by beat basis as discussed in the above cited patents, and this brings with it an additional opportunity for energy savings.

However, as discussed in the '646 application, even with this alternative mechanism for detecting loss of capture, the ability to perform a conventional capture management operations such as a threshold test or a safety margin check as described in the above-cited patents is still desirable. The present invention provides an improved stability check as a prerequisite to such a conventional threshold test or to a safety margin check.

The stability check according to the invention is believed beneficial in conjunction with capture management operations such as a simple safety margin test or a pacing threshold measurement. A simple safety margin check may, for example, comprise delivery of a single test cycle of support pulses at the programmed pulse amplitude followed by a test pulse at a lower amplitude to verify that the current pulse amplitude provides the required safety margin. A threshold measurement test may comprise a series of test cycles including test pulses at a variety of amplitudes to provide a more specific measurement of pacing threshold.

The stability check is performed while the pacemaker is operating in a conventional demand mode such as VVI AAI, etc. As is conventional in such pacing modes, the device defines refractory periods following sensed and paced events as described above. Unlike events sensed outside of these refractory periods, events sensed during the refractory periods typically do not re-start timing of the escape interval prior to a next delivered pacing pulse.

The pacing pulses during the stability check may be delivered at a preset stability check rate or may be delivered at the programmed base pacing rate of the device. During the stability check, the device measures intervals between paced and sensed events in the chamber being paced and determines whether the measured intervals are at a stable rate low enough to be reliably over-driven while performing a capture management operation such as a threshold test or a safety margin check In one embodiment of the present invention, during a first try of the stability check, the device examines a predetermined number of sequential ventricular paced (VP) and sensed (VS) events (e.g. 8 V-V events). If a) these events do not meet the criterion for a successful stability check; b) the device is not already at a defined available pacing output level; and c) f there is a short measured VP-VS in the 8 events, the device increases the pacing pulse amplitude and retries the stability check at the higher pacing pulse amplitude. The reason for this operation is that the presence of the short VP—VS interval raises the possibility that the stability criterion was not met due to non-capture of the delivered pacing pulses. Increasing the amplitude of the pacing pulses during a re-try of the stability check, if possible, reduces the likelihood that the re-tried stability check will fail due to non-capture.

The present invention is believed to be especially useful inte context of highly miniaturized pacemakers, such as those intended for implant entirely within or on a chamber of a patient's heart. As noted above, in such devices, it is desirable to employ a lower safety margin than is typically used in traditional pacemakers in order to reduce current drain and extend battery device. In such devices, the likelihood that a failure of a stability check will be due to non-capture rather than an unstable or too rapid intrinsic rhythm is correspondingly increased. The present invention provides a mechanism for dealing with this issue and facilitating the use of lower safety margins.

In one embodiment of the invention, for purposes of measuring the V-V intervals used in performance of the stability check, ventricular events sensed during the refractory periods (VSR) following paced events are not considered. The inventors have determined that ignoring these events in this embodiment of the invention is not problematic because in many cases, these VSR events will be due to over-sensing of T-waves, and in those cases in which they are due to an intrinsic rhythm not being captured by the pacing pulses, the intrinsic rhythm will still be detected as non-refractory events during the 8 measured intervals.

In this embodiment, if the patient has sufficient ectopic activity to have pacing capture followed by these sorts of VP-VS intervals, they are likely to fail the second attempt at the stability check as well, and there is no significant measurable longevity loss from delivering an additional 8 paces at the higher output amplitude. If a single premature ventricular contraction (PVC) during the first attempt of the stability check causes the retry of the stability check at the higher amplitude, a following threshold test is still likely to complete, with the resultant calculated pacing pulse amplitude most likely restored to its previous value.

In other embodiments of the invention, events sensed during the refractory periods may be considered in measuring the intervals used to perform the stability check. Further, while the specific embodiment discussed herein is directed to performing a stability check based upon measured ventricular intervals, the invention may also be usefully applied to assess stability using intervals between atrial sensed and paced events.

In addition to providing a stability check as a prerequisite to performance of a threshold test, the present invention also independently provides a quick check of whether the pacing pulses are presently capturing the heart. If the first try of the stability check contains VPs and no significantly early VS events, then it is reasonable to conclude that the present pacing pulse amplitude is adequate to capture the heart. If the stability check fails on the first try due to early VS events, but then passes on the second try once the amplitude is raised, it is reasonable to conclude that the pacing threshold is between the originally programmed amplitude and the newly raised amplitude. If the stability check fails on both the first and second tries due to early VS events, then it is reasonable to conclude that the pacing threshold is higher than the raised pulse amplitude.

This quick analysis of the pacing threshold as discussed above may be used several ways. First, it may be employed to provide information to the capture management process about the most likely pulse amplitude range in which to attempt testing. This potentially will allow a threshold test to run for a shorter duration, reducing energy expenditures associated with the test. Second, it may be employed to provide quick feedback to the user during implant about the implant location, potentially allowing them to more quickly gauge whether they want to run an entire threshold check at the present electrode location or simply move on to a different potential implant location. Use of the stability check as discussed above is correspondingly also beneficial in conjunction with optimization of atrial pacing threshold measurements and in conjunction with placement of electrodes in the atrium.

The present invention may be employed as part of or in conjunction with any of the various known capture management operations such as threshold tests and safety margin checks as discussed in the patents cited above. It may also be used in conjunction with alternative loss of capture mechanisms as described in the '646 application cited above. The invention is believed beneficial in the context of any pacing device that adjusts pacing pulse energy to maintain capture.

DETAILED DESCRIPTION

Figure 1:
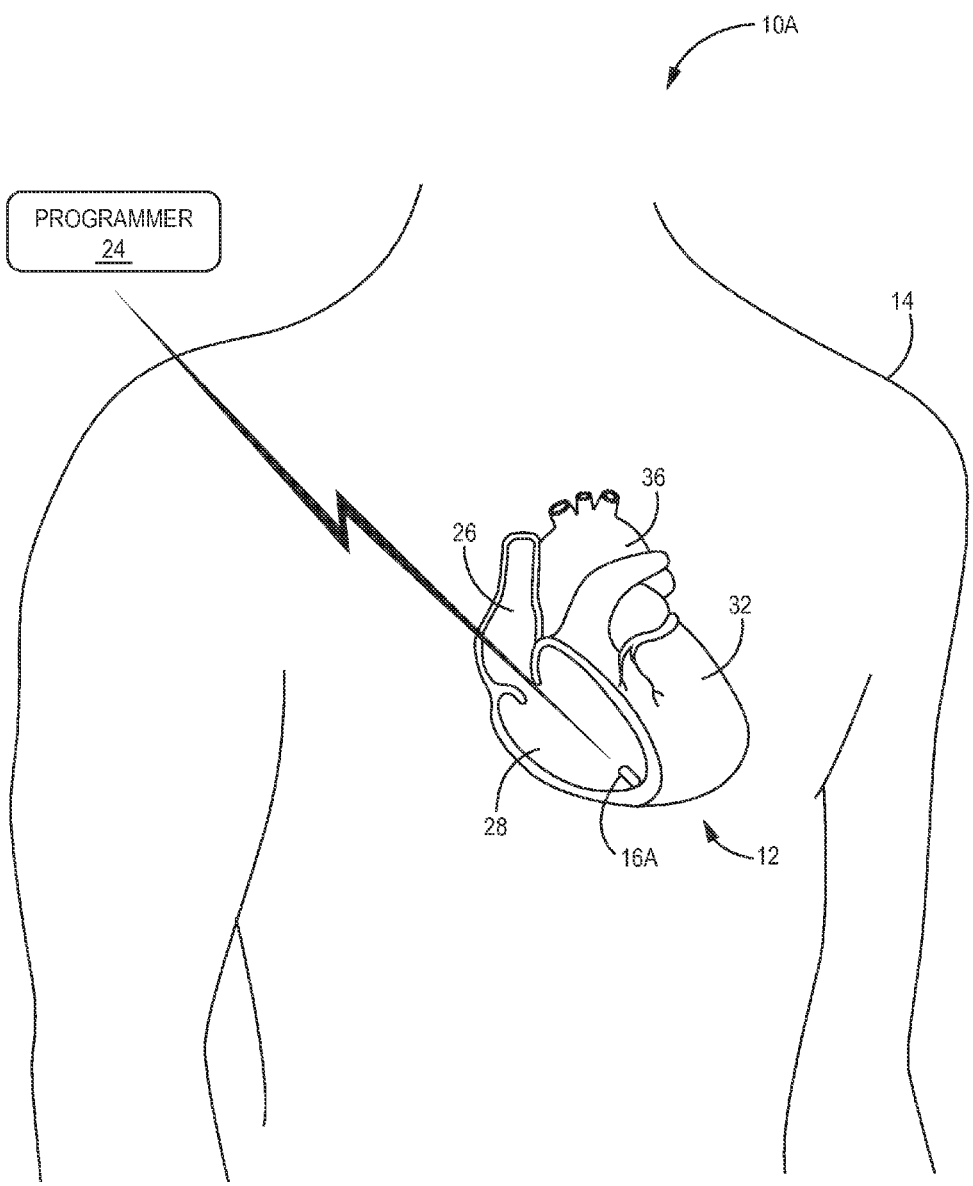
FIG. 1 is a diagram illustrating an example therapy system comprising a leadless implantable medical device (IMD) that may be used to monitor one or more physiological parameters of a patient and/or provide therapy to the heart of a patient.

FIG. 1 is a diagram illustrating an exemplary therapy system 10A that may be used to monitor one or more physiological parameters of patient 14 and/or to provide therapy to heart 12 of patient 14. Therapy system 10A includes an implantable medical device (IMD) 16A, which is coupled to programmer 24. IMD 16A may be an implantable leadless pacemaker that provides electrical signals to heart 12 via one or more electrodes (not shown in FIG. 1) on its outer housing. Additionally or alternatively, IMD 16A may sense electrical signals attendant to the depolarization and repolarization of heart 12 via electrodes on its outer housing. In some examples, IMD 16A provides pacing pulses to heart 12 based on the electrical signals sensed within heart 12. Patient 14 is ordinarily, but not necessarily, a human patient.

In the example of FIG. 1, IMD 16A is positioned wholly within heart 12 with one end proximate to the apex of right ventricle 28 to provide right ventricular (RV) pacing. Although IMD 16A is shown within heart 12 and proximate to the apex of right ventricle 28 in the example of FIG. 1, IMD 16A may be positioned at any other location outside or within heart 12. For example, IMD 16A may be positioned outside or within right atrium 26, left atrium 36, and/or left ventricle 32, e.g., to provide right atrial, left atrial, and left ventricular pacing, respectively. Depending in the location of implant, IMD 16A may include other stimulation functionalities. For example, IMD 16A may provide atrioventricular nodal stimulation, fat pad stimulation, vagal stimulation, or other types of neurostimulation. In other examples, IMD 16A may be a monitor that senses one or more parameters of heart 12 and may not provide any stimulation functionality. In some examples, system 10A may include a plurality of leadless IMDs 16A, e.g., to provide stimulation and/or sensing at a variety of locations.

FIG. 1 further depicts programmer 24 in communication with IMD 16A. In some examples, programmer 24 comprises a handheld computing device, computer workstation, or networked computing device. Programmer 24 includes a user interface that presents information to and receives input from a user. It should be noted that the user may also interact with programmer 24 remotely via a networked computing device.

A user, such as a physician, technician, surgeon, electrophysiologist, other clinician, or patient, interacts with programmer 24 to communicate with IMD 16A. For example, the user may interact with programmer 24 to retrieve physiological or diagnostic information from IMD 16A. A user may also interact with programmer 24 to program IMD 16A, e.g., select values for operational parameters of the IMD 16A. For example, the user may use programmer 24 to retrieve information from IMD 16A regarding the rhythm of heart 12, trends therein over time, or arrhythmic episodes.

As another example, the user may use programmer 24 to retrieve information from IMD 16A regarding other sensed physiological parameters of patient 14 or information derived from sensed physiological parameters, such intracardiac or intravascular pressure, activity, posture, respiration, tissue perfusion, heart sounds, cardiac electrogram (EGM), intracardiac impedance, or thoracic impedance. In some examples, the user may use programmer 24 to retrieve information from IMD 16A regarding the performance or integrity of IMD 16A or other components of system 10A, or a power source of IMD 16A. As another example, the user may interact with programmer 24 to program, e.g., select parameters for, therapies provided by IMD 16A, such as pacing and, optionally, neurostimulation.

IMD 16A and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16A implant site in order to improve the quality or security of communication between IMD 16A and programmer 24.

Figure 2:
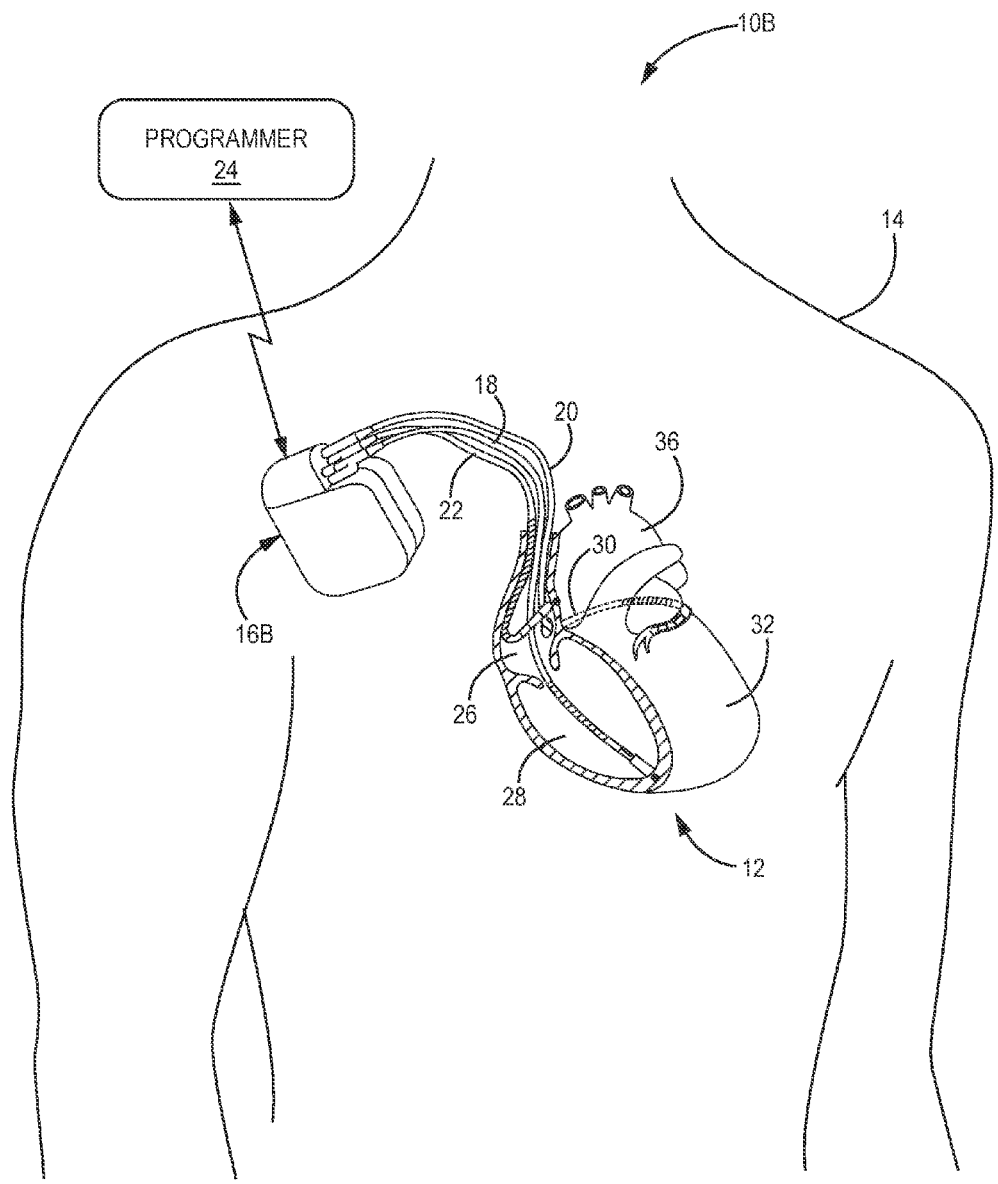
FIG. 2 is a diagram illustrating another example therapy system comprising an IMD coupled to a plurality of leads that may be used to monitor one or more physiological parameters of a patient and/or provide therapy to the heart of a patient.

FIG. 2 is a diagram illustrating another exemplary therapy system 10B that may be used to monitor one or more physiological parameters of patient 14 and/or to provide therapy to heart 12 of patient 14. Therapy system 10B includes IMD 16B, which is coupled to leads 18, 20, and 22, and programmer 24. In one example, IMD 16B may be an implantable pacemaker that provides electrical signals to heart 12 via electrodes coupled to one or more of leads 18, 20, and 22. In addition to pacing therapy, IMD 16B may deliver neurostimulation signals. In some examples, IMD 16B may also include cardioversion and/or defibrillation functionalities. In other examples, IMD 16B may not provide any stimulation functionalities and, instead, may be a dedicated monitoring device. Patient 14 is ordinarily, but not necessarily, a human patient.

Leads 18, 20, 22 extend into the heart 12 of patient 14 to sense electrical activity of heart 12 and/or deliver electrical stimulation to heart 12. In the example shown in FIG. 2, right ventricular (RV) lead 18 extends through one or more veins (not shown), the superior vena cava (not shown), right atrium 26, and into right ventricle 28. RV lead 18 may be used to deliver RV pacing to heart 12. Left ventricular (LV) lead 20 extends through one or more veins, the vena cava, right atrium 26, and into the coronary sinus 30 to a region adjacent to the free wall of left ventricle 32 of heart 12. LV lead 20 may be used to deliver LV pacing to heart 12. Right atrial (RA) lead 22 extends through one or more veins and the vena cava, and into the right atrium 26 of heart 12. RA lead 22 may be used to deliver RA pacing to heart 12.

In some examples, system 10B may additionally or alternatively include one or more leads or lead segments (not shown in FIG. 2) that deploy one or more electrodes within the vena cava or other vein, or within or near the aorta. Furthermore, in another example, system 10B may additionally or alternatively include one or more additional intravenous or extravascular leads or lead segments that deploy one or more electrodes epicardially, e.g., near an epicardial fat pad, or proximate to the vagus nerve. In other examples, system 10B need not include one of ventricular leads 18 and 20.

IMD 16B may sense electrical signals attendant to the depolarization and repolarization of heart 12 via electrodes (described in further detail with respect to FIG. 4) coupled to at least one of the leads 18, 20, 22. In some examples, IMD 16B provides pacing pulses to heart 12 based on the electrical signals sensed within heart 12. The configurations of electrodes used by IMD 16B for sensing and pacing may be unipolar or bipolar.

IMD 16B may also provide neurostimulation therapy, defibrillation therapy and/or cardioversion therapy via electrodes located on at least one of the leads 18, 20, 22. For example, IMD 16B may deliver defibrillation therapy to heart 12 in the form of electrical pulses upon detecting ventricular fibrillation of ventricles 28 and 32. In some examples, IMD 16B may be programmed to deliver a progression of therapies, e.g., pulses with increasing energy levels, until a fibrillation of heart 12 is stopped. As another example, IMD 16B may deliver cardioversion or ATP in response to detecting ventricular tachycardia, such as tachycardia of ventricles 28 and 32.

As described above with respect to IMD 16A of FIG. 1, programmer 24 may also be used to communicate with IMD 16B. In addition to the functions described with respect to IMD 16A of FIG. 1, a user may use programmer 24 to retrieve information from IMD 16B regarding the performance or integrity of leads 18, 20 and 22 and may interact with programmer 24 to program, e.g., select parameters for, any additional therapies provided by IMD 16B, such as cardioversion and/or defibrillation.

In addition to the functions described with respect to IMD 16A of FIG. 1, a user may use programmer 24 to retrieve information from IMD 16B regarding the performance or integrity of leads 18, 20 and 22 and may interact with programmer 24 to program, e.g., select parameters for, any additional therapies provided by IMD 16B, such as cardioversion and/or defibrillation.

Figure 3:
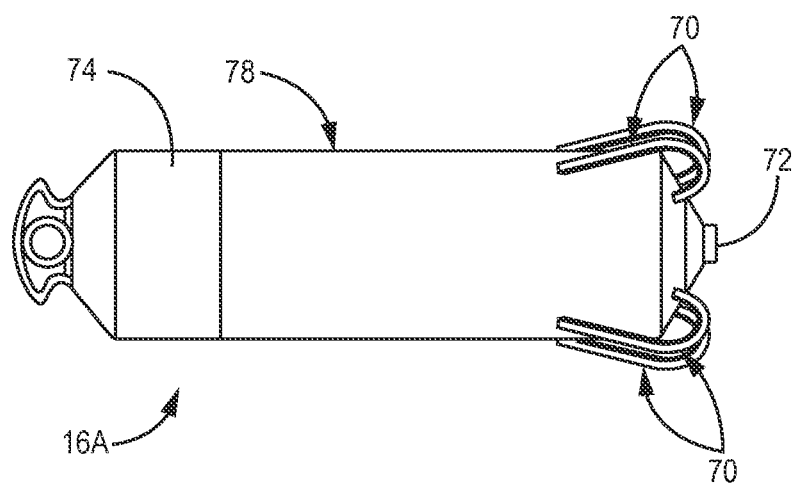
FIG. 3 illustrates the IMD of FIG. 1 in more detail

FIG. 3 is a diagram illustrating leadless IMD 16 of FIG. 1 in further detail. In the example of FIG. 3, leadless IMD 16A includes fixation mechanism 70. Fixation mechanism 70 may anchor leadless IMD 16A to a wall of heart 12. For example, fixation mechanism 70 may take the form of multiple tines that may be inserted into a wall of heart 12 to fix leadless IMD 16A at the apex of right ventricle 28. Alternatively, other structures of fixation mechanism 70, e.g., adhesive, sutures, or screws may be utilized. In some examples, fixation mechanism is conductive and may be used as an electrode, e.g., to deliver therapeutic electrical signals to heart 12 and/or sense intrinsic depolarizations of heart 12.

Leadless IMD 16A may also include electrodes 72 and 74 at a tip of outer housing 78. Electrodes 72 and 74 may be used to deliver therapeutic electrical signals to heart 12 and/or sense intrinsic depolarizations of heart 12. Electrodes 72 and 74 may be formed integrally with an outer surface of hermetically-sealed housing 78 of IMD 16A or otherwise coupled to housing 78. In this manner, electrodes 72 and 74 may be referred to as housing electrodes. In some examples, housing electrodes 72 and 74 are defined by uninsulated portions of an outward facing portion of housing 78 of IMD 16A. Other division between insulated and uninsulated portions of housing 78 may be employed to define a different number or configuration of housing electrodes. For example, in an alternative configuration, IMD 16A may include a single housing electrode that comprises substantially all of housing 78, and may be used in combination with an electrode formed by fixation mechanism 70 for sensing and/or delivery of therapy.

Figure 4:
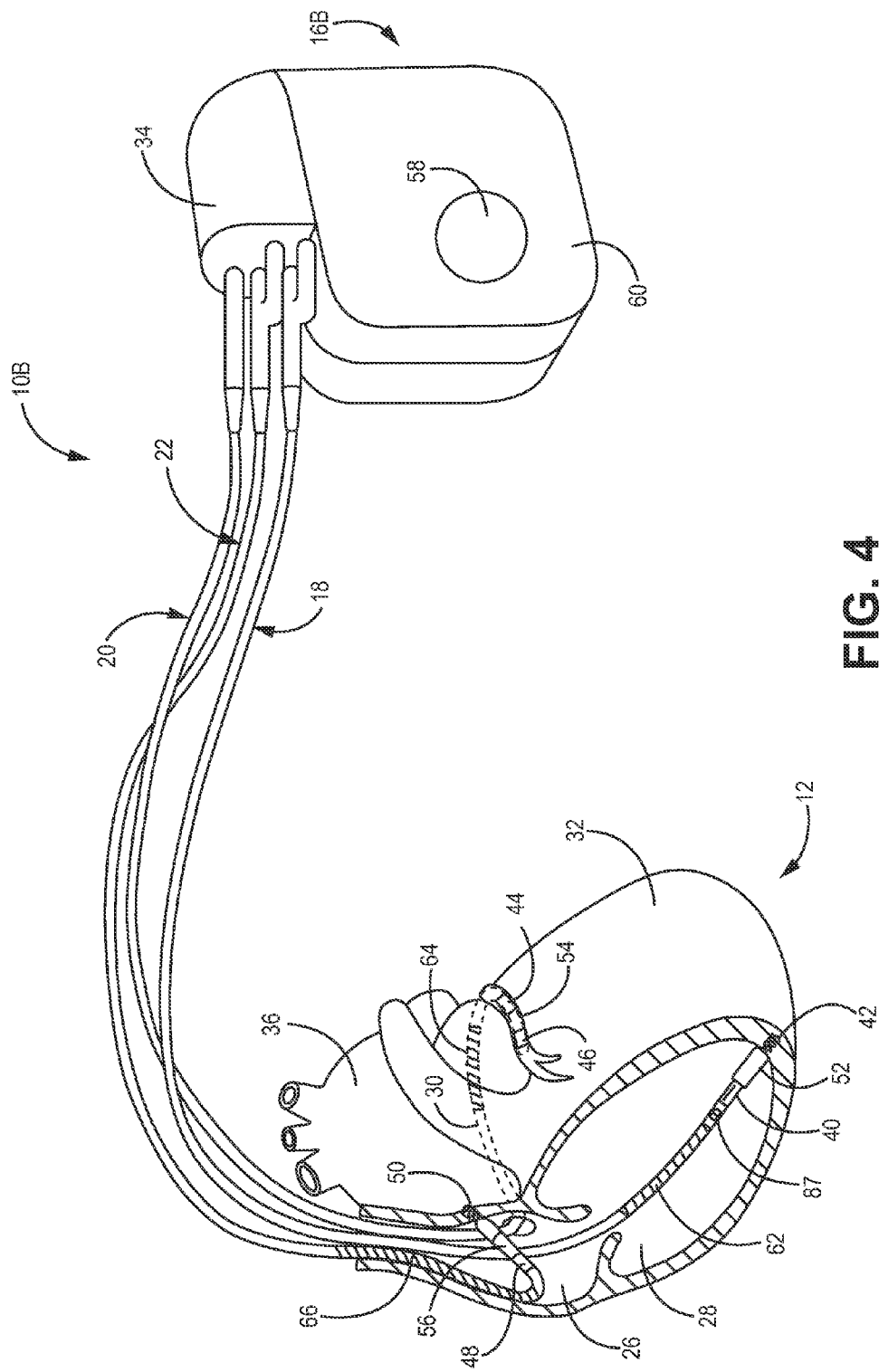
FIG. 4 illustrates the IMD of FIG. 2 in more detail

FIG. 4 is a diagram illustrating IMD 16B and leads 18, 20, 22 of therapy system 10B of FIG. 2 in greater detail. Leads 18, 20, 22 may be electrically coupled to a signal generator and a sensing module of IMD 16B via connector block 34. In some examples, proximal ends of leads 18, 20, 22 may include electrical contacts that electrically couple to respective electrical contacts within connector block 34 of IMD 16B. In some examples, a single connector, e.g., an IS-4 or DF-4 connector, may connect multiple electrical contacts to connector block 34. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in left ventricle 32 and bipolar electrodes 48 and 50 are located adjacent to a distal end of lead 22 in right atrium 26. In the illustrated example, there are no electrodes located in left atrium 36. However, other examples may include electrodes in left atrium 36.

Electrodes 40, 44, and 48 may take the form of ring electrodes, and electrodes 42, 46, and 50 may take the form of extendable helix tip electrodes mounted retractably within insulative electrode heads 52, 54, and 56, respectively. In some examples, one or more of electrodes 42, 46, and 50 may take the form of pre-exposed helix tip electrodes. In other examples, one or more of electrodes 42, 46, and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64, and 66 may be electrically coupled to a respective one of the coiled conductors within the lead body of its associated lead 18, 20, 22, and thereby coupled to respective ones of the electrical contacts on the proximal end of leads 18, 20, 22.

In some examples, as illustrated in FIG. 4, IMD 16B includes one or more housing electrodes, such as housing electrode 58, which may be formed integrally with an outer surface of hermetically-sealed housing 60 of IMD 16B or otherwise coupled to housing 60. In some examples, housing electrode 58 is defined by an uninsulated portion of an outward facing portion of housing 60 of IMD 16B. Other division between insulated and uninsulated portions of housing 60 may be employed to define two or more housing electrodes. In some examples, housing electrode 58 comprises substantially all of housing 60.

IMD 16B may sense electrical signals attendant to the depolarization and repolarization of heart 12 via electrodes 40, 42, 44, 46, 48, 50, 58, 62, 64, and 66. The electrical signals are conducted to IMD 16B from the electrodes via conductors within the respective leads 18, 20, 22 or, in the case of housing electrode 58, a conductor coupled to housing electrode 58. IMD 16B may sense such electrical signals via any bipolar combination of electrodes 40, 42, 44, 46, 48, 50, 58, 62, 64, and 66. Furthermore, any of the electrodes 40, 42, 44, 46, 48, 50, 58, 62, 64, and 66 may be used for unipolar sensing in combination with housing electrode 58.

In some examples, IMD 16B delivers pacing pulses via bipolar combinations of electrodes 40, 42, 44, 46, 48 and 50 to produce depolarization of cardiac tissue of heart 12. In some examples, IMD 16B delivers pacing pulses via any of electrodes 40, 42, 44, 46, 48 and 50 in combination with housing electrode 58 in a unipolar configuration.

Furthermore, IMD 16B may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes.

The configuration of the systems illustrated in FIGS. 1-4 are merely exemplary. In other examples, a system may include percutaneous leads, epicardial leads and/or patch electrodes instead of or in addition to the transvenous leads 18 and 22 illustrated in FIG. 2. Further, the IMD need not be implanted within patient 14. In examples in which the IMD is not implanted in a patient, the IMD may deliver defibrillation pulses and other therapies to heart 12 via percutaneous leads that extend through the skin of patient 14 to a variety of positions within or outside of heart 12.

In addition, in other examples, a system may include any suitable number of leads coupled to IMD 16B, and each of the leads may extend to any location within or proximate to heart 12. For example, other examples of systems may include three transvenous leads located as illustrated in FIGS. 2 and 4, and an additional lead located within or proximate to left atrium 36. Other examples of systems may include a single lead that extends from IMD 16B into right atrium 26 or right ventricle 28, or two leads that extend into a respective one of the right ventricle 26 and right atrium 26. Any electrodes located on these additional leads may be used in sensing and/or stimulation configurations.

Figure 5:
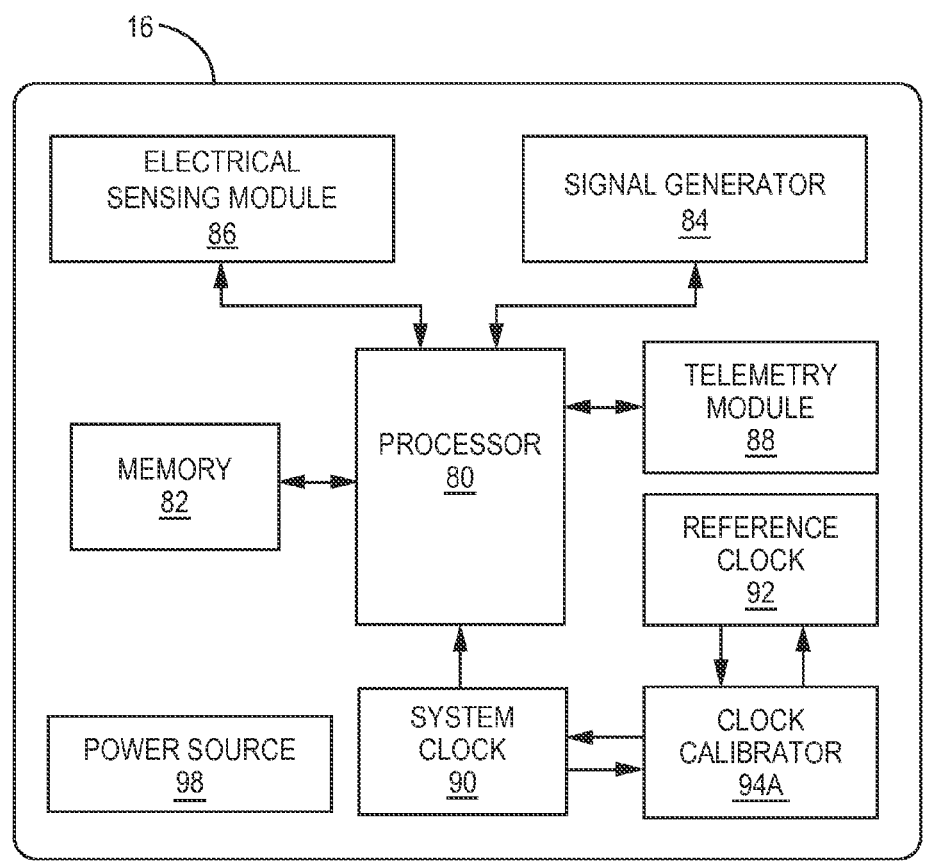
FIG. 5 is a functional block diagram illustrating an example configuration of an IMD.

FIG. 5 is a functional block diagram illustrating an example configuration of IMD 16, which may be IMD 16A of FIGS. 1 and 3 or IMD 16B of FIGS. 2 and 4. In the example illustrated by FIG. 4, IMD 16 includes a processor 80, memory 82, signal generator 84, electrical sensing module 86, telemetry module 88, system clock 90, reference clock 92, clock calibrator 94A, and power source 98. Memory 82 may include computer-readable instructions that, when executed by processor 80, cause IMD 16 and processor 80 to perform various functions attributed to IMD 16 and processor 80 herein. Memory 82 may comprise a computer-readable storage medium, including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog storage media.

Figure 6:
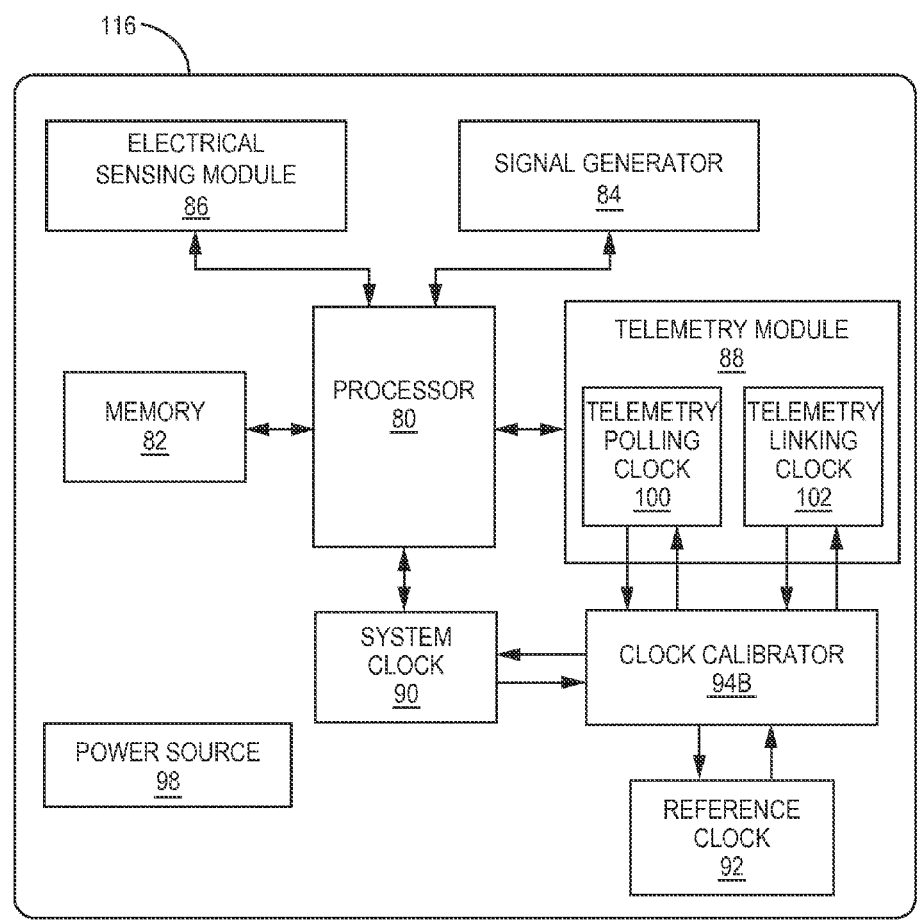
FIG. 6 is a block diagram of an example external programmer that facilitates user communication with an IMD.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 in this disclosure may be embodied as software, firmware, hardware or any combination thereof. IMD 16 also includes a sensing integrity module 90, as illustrated in FIG. 6, which may be implemented by processor 80, e.g., as a hardware component of processor 80, or a software component executed by processor 80.

Processor 80 controls signal generator 84 to deliver stimulation therapy to heart 12 according to operational parameters or programs, which may be stored in memory 82. For example, processor 80 may control signal generator 84 to deliver electrical pulses with the amplitudes, pulse widths, frequency, or electrode polarities specified by the selected one or more therapy programs.

In the particular case of cardiac pacing, intervals controlled by the processor 80 would typically include the pacing rate (escape interval duration), refractory periods during which sensed depolarization events do not reset timing of the escape interval, blanking periods during which depolarization events are not sensed.

Signal generator 84, as well as electrical sensing module 86, is electrically coupled to electrodes of IMD 16 and/or leads coupled to IMD 16. In the example of leadless IMD 16A of FIG. 3, signal generator 84 and electrical sensing module 86 are coupled to electrodes 72 and 74, e.g., via conductors disposed within housing 78 of leadless IMD 16A. In examples in which fixation mechanism 70 functions as an electrode, signal generator 84 and electrical sensing module 86 may also be coupled to fixation mechanism 70, e.g., via a conductor disposed within housing 78 of leadless IMD 16A. In the example of IMD 16B of FIG. 2, signal generator 84 and electrical sensing module 86 are coupled to electrodes 40, 42, 48, 50, 56 and 62 via conductors of the respective lead 18 or 22, or, in the case of housing electrode 58, via an electrical conductor disposed within housing 60 of IMD 16B.

In the example illustrated in FIG. 4, signal generator 84 is configured to generate and deliver electrical stimulation therapy to heart 12. For example, signal generator 84 may deliver pacing, cardioversion, defibrillation, and/or neurostimulation therapy via at least a subset of the available electrodes. In some examples, signal generator 84 delivers one or more of these types of stimulation in the form of electrical pulses. In other examples, signal generator 84 may deliver one or more of these types of stimulation in the form of other signals, such as sine waves, square waves, or other substantially continuous time signals.

Signal generator 84 may include a switch module and processor 80 may use the switch module to select, e.g., via a data/address bus, which of the available electrodes are used to deliver stimulation signals, e.g., pacing, cardioversion, defibrillation, and/or neurostimulation signals. The switch module may include a switch array, switch matrix, multiplexer, or any other type of switching device suitable to selectively couple a signal to selected electrodes.

Electrical sensing module 86 monitors signals from at least a subset of the available electrodes in order to monitor electrical activity of heart 12. Electrical sensing module 86 may also include a switch module to select which of the available electrodes are used to sense the heart activity. In some examples, processor 80 may select the electrodes that function as sense electrodes, i.e., select the sensing configuration, via the switch module within electrical sensing module 86, e.g., by providing signals via a data/address bus.

In some examples, electrical sensing module 86 includes multiple detection channels, each of which may comprise an amplifier. Each sensing channel may detect electrical activity in respective chambers of heart 12, and may be configured to detect either R-waves or P-waves. In some examples, electrical sensing module 86 or processor 80 may include an analog-to-digital converter for digitizing the signal received from a sensing channel for electrogram (EGM) signal processing by processor 80. In response to the signals from processor 80, the switch module within electrical sensing module 86 may couple the outputs from the selected electrodes to one of the detection channels or the analog-to-digital converter.

During pacing, escape interval counters maintained by processor 80 may be reset upon sensing of R-waves and P-waves with respective detection channels of electrical sensing module 86. Signal generator 84 may include pacer output circuits that are coupled, e.g., selectively by a switching module, to any combination of the available electrodes appropriate for delivery of a bipolar or unipolar pacing pulse to one or more of the chambers of heart 12. Processor 80 may control signal generator 84 to deliver a pacing pulse to a chamber upon expiration of an escape interval. Processor 80 may reset the escape interval counters upon the generation of pacing pulses by signal generator 84, or detection of an intrinsic depolarization in a chamber, and thereby control the basic timing of cardiac pacing functions. The escape interval counters may include P-P, V-V, RV-LV, A-V, A-RV, or A-LV interval counters, as examples. The value of the count present in the escape interval counters when reset by sensed R-waves and P-waves may be used by processor 80 to measure the durations of R-R intervals, P-P intervals, P-R intervals and R-P intervals. Processor 80 may use the count in the interval counters to detect heart rate, such as an atrial rate or ventricular rate.

In the particular context of the present invention, the processor also determines intervals between successive sensed and paced events in a given chamber. For example, in the case in which the invention is embodied in a ventricular pacemaker, the processor would calculate V-pace to V-pace intervals, V-sense to V-sense intervals, V-pace to V-sense intervals and V-sense to V-pace intervals. The processor 80 stores these intervals in memory 82 for analysis according to the present invention.

Operation of the present invention to perform the stability check will typically be controlled and defined by software instructions stored in memory 82 and implemented by processor 80. Such instructions would correspond to the functional flow-charts of FIG. 8, discussed below.

Telemetry module 88 includes any suitable hardware, firmware, software or any combination thereof for communicating with another device, such as programmer 24 (FIGS. 1 and 2). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and receive downlinked data from programmer 24 via an address/data bus. In some examples, telemetry module 88 may provide received data to processor 80 via a multiplexer.

The clocking system of IMD 16 includes system clock 90, reference clock 92, and clock calibrator 94A. Each of the clocks described herein comprise oscillators that may operate at different frequencies with different accuracies and different power requirements. IMD 16 may require an extremely small housing form factor, especially in the case of leadless IMD 16A of FIGS. 1 and 3. For example, leadless IMD 16 may have a form factor of less than 1 cubic centimeter. Due to the small form factor requirements, IMD 16 may only be able to accommodate a small battery canister such that current drain within IMD 16 must by extremely low. One aspect of reducing power in IMD 16 is to minimize current drain by the clocking system.

A detailed description of the use of the clocking system to reduce power consumption is set forth in US Patent Publication No. US 20120109259 A1, incorporated herein by reference in its entirety FIG. 6 is a functional block diagram of an example configuration of programmer 24. As shown in FIG. 12, programmer 24 includes processor 140, memory 142, user interface 144, telemetry module 146, and power source 148. Programmer 24 may be a dedicated hardware device with dedicated software for programming of IMD 16. Alternatively, programmer 24 may be an off-the-shelf computing device running an application that enables programmer 24 to program IMD 16. In other examples, programmer 24 may be used to program IMD 16 of FIG. 7 in a substantially similar manner as IMD 16 of FIG. 6.

A user may use programmer 24 to select therapy programs (e.g., sets of stimulation parameters), generate new therapy programs, or modify therapy programs for IMD 16. The clinician may interact with programmer 24 via user interface 144, which may include a display to present a graphical user interface to a user, and a keypad or another mechanism for receiving input from a user.

Processor 140 can take the form one or more microprocessors, DSPs, ASICs, FPGAs, programmable logic circuitry, or the like, and the functions attributed to processor 140 in this disclosure may be embodied as hardware, firmware, software or any combination thereof. Memory 142 may store instructions and information that cause processor 140 to provide the functionality ascribed to programmer 24 in this disclosure. Memory 142 may include any fixed or removable magnetic, optical, or electrical media, such as RAM, ROM, CD-ROM, hard or floppy magnetic disks, EEPROM, or the like. Memory 142 may also include a removable memory portion that may be used to provide memory updates or increases in memory capacities. A removable memory may also allow patient data to be easily transferred to another computing device, or to be removed before programmer 24 is used to program therapy for another patient. Memory 142 may also store information that controls therapy delivery by IMD 16, such as stimulation parameter values.

Programmer 24 may communicate wirelessly with IMD 16, such as using RF communication or proximal inductive interaction. This wireless communication is possible through the use of telemetry module 146, which may be coupled to an internal antenna or an external antenna. An external antenna that is coupled to programmer 24 may correspond to the programming head that may be placed over heart 12, as described above with reference to FIG. 1. Telemetry module 146 may be similar to telemetry module 88 of IMD 16 (FIG. 6).

Telemetry module 146 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

Figure 7:
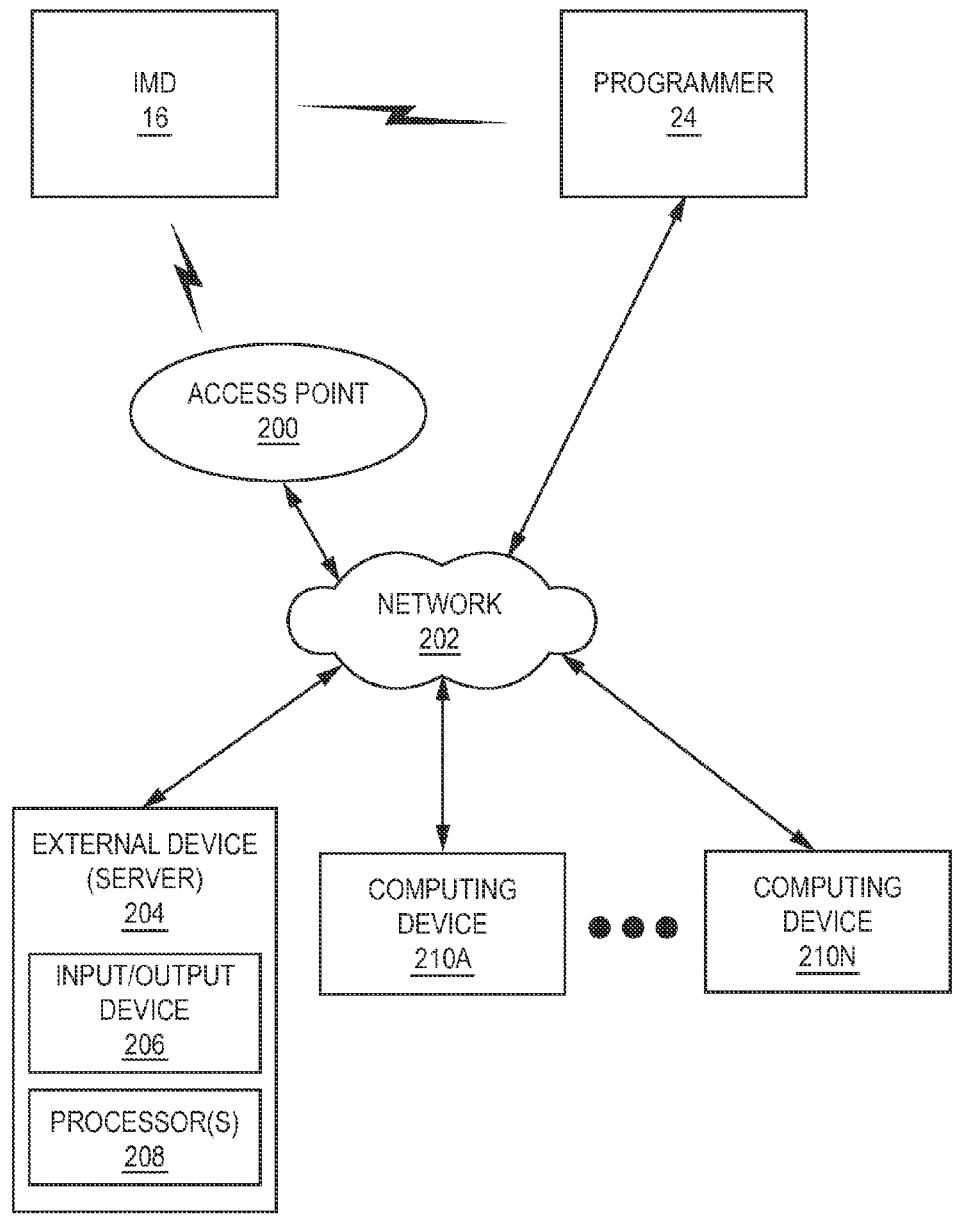
FIG. 7 is a block diagram illustrating an example system that includes an external device, such as a server, and one or more computing devices that are coupled to an IMD and programmer via a network.

FIG. 7 is a block diagram illustrating an example system that includes an external device, such as a server 204, and one or more computing devices 210A-210N, that are coupled to the IMD 16 and programmer 24 (shown in FIGS. 1 and 2) via a network 202. In other examples, the system of FIG. 13 may include IMD 116 of FIG. 7 in a substantially similar manner as IMD 16 of FIG. 6.

In this example, IMD 16 may use its telemetry module 88 to communicate with programmer 24 via a first wireless connection, and to communication with an access point 200 via a second wireless connection. In the example of FIG. 13, access point 200, programmer 24, server 204, and computing devices 210A-210N are interconnected, and able to communicate with each other, through network 202. In some cases, one or more of access point 200, programmer 24, server 204, and computing devices 210A-210N may be coupled to network 202 through one or more wireless connections. IMD 16, programmer 24, server 204, and computing devices 210A-210N may each comprise one or more processors, such as one or more microprocessors, DSPs, ASICs, FPGAs, programmable logic circuitry, or the like, that may perform various functions and operations, such as those described herein.

Access point 200 may comprise a device that connects to network 202 via any of a variety of connections, such as telephone dial-up, digital subscriber line (DSL), or cable modem connections. In other examples, access point 200 may be coupled to network 202 through different forms of connections, including wired or wireless connections. In some examples, access point 200 may be co-located with patient 14 and may comprise one or more programming units and/or computing devices (e.g., one or more monitoring units) that may perform various functions and operations described herein. For example, access point 200 may include a home-monitoring unit that is co-located with patient 14 and that may monitor the activity of IMD 16. In some examples, server 204 or computing devices 210 may control or perform any of the various functions or operations described herein.

In some cases, server 204 may be configured to provide a secure storage site for data that has been collected from IMD 16 and/or programmer 24. Network 202 may comprise a local area network, wide area network, or global network, such as the Internet. In some cases, programmer 24 or server 206 may assemble data in web pages or other documents for viewing by trained professionals, such as clinicians, via viewing terminals associated with computing devices 210A-210N. The illustrated system of FIG. 13 may be implemented, in some aspects, with general network technology and functionality similar to that provided by the Medtronic CareLink® Network developed by Medtronic, Inc., of Minneapolis, Minn.

In one or more examples, the functions described above may be implemented in hardware, software, firmware, or any combination thereof. If implemented in software, the functions may be stored on or transmitted over as one or more instructions or code on a computer-readable medium. Computer-readable media may include computer data storage media or communication media including any medium that facilitates transfer of a computer program from one place to another. Data storage media may be any available media that can be accessed by one or more computers or one or more processors to retrieve instructions, code and/or data structures for implementation of the techniques described in this disclosure. By way of example, and not limitation, such computer-readable media can comprise RAM, ROM, EEPROM, CD-ROM or other optical disk storage, magnetic disk storage, or other magnetic storage devices, flash memory, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

The code may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules. Also, the techniques could be fully implemented in one or more circuits or logic elements.

Operation of preferred embodiments of the present invention is described below in conjunction with FIG. 8. The specific embodiments described are directed to a stability check in a ventricular pacemaker, but the same mechanism may be employed to check stability in atrial pacemakers as well. The embodiments of FIG. 8 should thus be considered exemplary rather than limiting with regard to the invention as claimed.

The stability check evaluates the patient's current rate, rhythm and device state to determine if a threshold test, safety margin check or other similar capture management operation can usefully proceed. During such capture management operations, as described in the references cited above, the device will typically proceed through one or more test cycles. In each test cycle, the device will deliver support pulses at a test rate which over-drives the patient's intrinsic rate, followed by a a lower amplitude test pulse. The device will then look for capture or loss of capture by the test pulse in a capture detect window thereafter. The support and test pulses are overdriven to ensure that intrinsic ventricular events do not fall in the capture detect window. The stability check verifies that the patient's rate is both stable at a rate low enough to safely overdrive the intrinsic rhythm. As noted above, the stability check according to the invention is believed beneficial in conjunction with either a simple safety margin test or in conjunction with pacing threshold measurement. A simple safety margin check may comprise delivery of a single test cycle of support pulses at the programmed pulse amplitude followed by a test pulse at a lower amplitude to verify that the programmed amplitude provides the required safety margin. A threshold measurement may comprise a series of test cycles including test pulses at a variety of amplitudes to provide a more specific measurement of pacing threshold.

If the stability check is successful, a test cycle or cycles will proceed. The pacing threshold and/or safety margin checks may correspond to any of the tests described in the above-cited patents. Operation of the stability test is described in conjunction with the flow chart of FIG. 8. FIG. 8 sets forth the basic structure of an instruction set stored in the memory of the device as described above and executed by the microprocessor therein.

Figure 8:
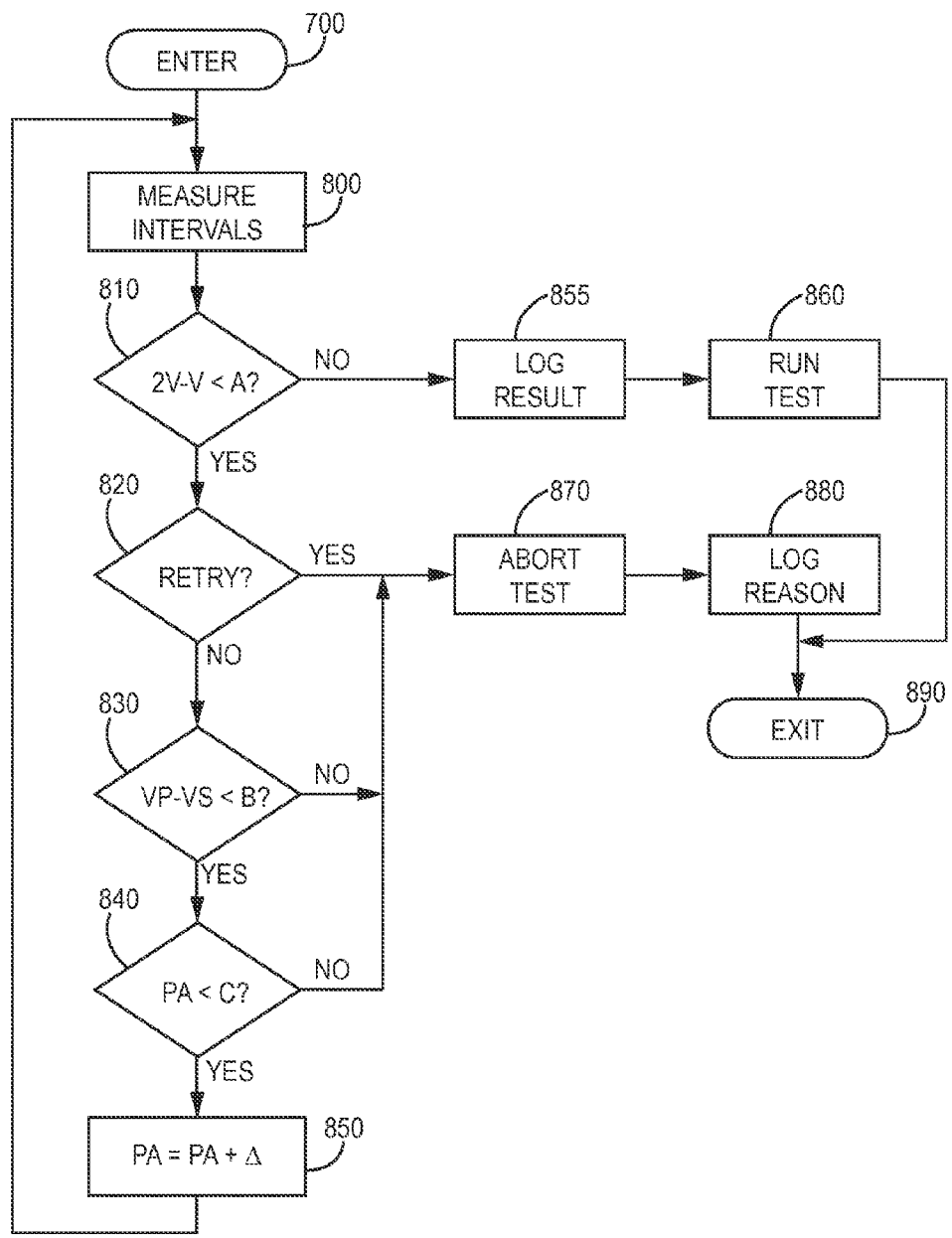
FIG. 8 is a flow chart illustrating the operation of the invention.

In the specific case illustrated in FIG. 8—if multiple test cycles are to be run, the illustrated embodiment provides that the stability check is run before each test cycle to verify that the patient's intrinsic rate is still low enough for the next scheduled test cycle to proceed. In alternative embodiments, multiple test cycles may follow a single stability check. As discussed below, in conjunction with some applications of the present invention, such as during initial implant, the stability check can be performed as a stand-alone test to provide a quick check as to the suitability of an implant location.

For purposes of the following description, a V-V interval includes intervals between successive ventricular sensed event s (VS—VS), intervals between paced ventricular events and subsequent sensed events (VP—VS), intervals between sensed ventricular events and subsequent paced events (VS—VP) and intervals between successive paced events (VP—VP). In a preferred embodiment, the first try of the stability check may be performed at the current effective pacing pulse amplitude. As discussed below, the amplitude of the delivered stability check pulses may vary during the process of threshold testing.

The stability check may be initiated at 700 by programming command, or responsive to a scheduled occurrence of a test cycle as discussed above. The stability check may be re-initiated prior to each scheduled threshold test cycle.

During a stability check or stability check retry, at 800 the device measures up to a preset number (e.g. 8) of successive intervals between ventricular events (V—V intervals). As discussed above, in some embodiments, the ventricular events considered will not include refractory ventricular sensed vents (VSRs). As noted above, the V-V intervals are measured while the pacemaker is operating in a conventional demand mode such as VVI AAI, etc. As is conventional in such pacing modes, the device defines refractory periods following sensed and paced events as described above.

If less than two (or other predetermined number) of these measured intervals are less than a predetermined minimum interval "A" at 810, the device logs a successful stability check at 855 and enables a test cycle at 860. In this circumstance, the stability criterion is met. The minimum interval "A" is preferably chosen as a function of the rate of the support and test pulses to be delivered during the test cycle, and may correspond to the rate of or intervals between these pulses, minus or plus a delta, respectively.

If at least two measured V-V intervals are less than the predetermined minimum interval "A" at 810, the device checks at 820 to determine whether the stability check underway is a stability check retry. If so, the threshold test is aborted at 870, and the reason for the test abort is logged at 880 and the device returns to normal operation at 890.

If the stability check underway is not a stability check retry at 820 (i.e. it is the first try) the device checks at 830 to determine whether a measured VP-VS interval not including Refractory Ventricular Senses is less than defined duration "B". In preferred embodiments, "B" can be chosen as a function of the intervals between the overdrive support and test pulses in the scheduled test cycle. For example, "B" may be equal to such an interval plus or minus a delta. Occurrence of such a short VP-VS interval is taken as an indication of a possible loss of capture.

If no such short VP—VS interval occurs, the device concludes that the failure of the first try of the stability check was likely not due to a loss of capture and therefore aborts the test cycle at 870 and logs the reason for the test cycle abort at 880. If such a short VP—VS interval is present, the device determines that the failure of the first try of the stability check may have been due to a loss of capture.

If the failure of first try of the stability check is determined to possibly be due to loss of capture, the device checks at 840 to determine whether the stability check can be usefully re-tried at a higher pulse amplitude. This may be done by determining whether the present pacing pulse amplitude is less than a defined value "C". The value of "C" is may be chosen depending upon the operation of the threshold test. For example, "C" may be the maximum available pulse amplitude, the scheduled test pace pulse amplitude plus a delta (e.g. 2 volts) or may be the lesser of the two. If the present pulse amplitude is less "C", the present pulse amplitude pulse amplitude is incremented at 850, and a retry of the stability check is undertaken at 800 and 810. The increased amplitude of the pacing pulses delivered in the re-try of the stability check is intended to reduce the possibility that the stability check will fail due to loss of capture. Otherwise, the scheduled test cycle will be aborted at 870, the reason for the aborted test cycle will be logged at 880 and the device will return to normal operation at 890.

If the stability check is re-tried and is successful at 810, the result is logged at 855 and the test cycle is performed at 860. If the stability check fails at 810, the device determines that the stability check is a re-try at 820, the scheduled test cycle is aborted at 870, the reason for the aborted test cycle is logged at 880 and the device returns to normal operation at 890.

The results of the stability check in some embodiments may be used to adjust the parameters in a test cycle following a successful first try or second try of the stability check. For example, if the first try of the stability check is successful, the support pacing pulses may be delivered at a first value, e.g. the programmed pulse amplitude. If the second try of the stability check is successful, the support pacing pulses may be delivered at a second value, e.g. the increased pulse amplitude as set at 850.

Additionally, in some embodiments, the results of the stability check may be used to adjust the amplitudes of the test pulses delivered during a threshold check. For example, the first test pulse in the first test cycle of the threshold check process may be delivered at a lower amplitude following a successful first try of the stability check and at a higher amplitude following a successful re-try of the stability check.

In this fashion, the number of test cycles required to determine the pacing threshold may be reduced.

Finally, in some embodiments the stability check can be employed as a stand-alone feature. For example, the stability check can be used as set forth below conjunction with the process of implanting the device. This aspect of the invention is particularly useful in the context of a device such as a miniaturized pacemaker located completely in or on a chamber of the patient's heart. In such devices, testing of potential implant locations is of typically done using the device itself under control of a programmer as described above.

In such case, after locating a pacing electrode of the device at a potential site, the programmer may instruct the pacemaker to perform a stability check according to the invention. In this case, a threshold test is not necessarily automatically initiated following the stability check. The logged results of the stability check may simply be telemetered to the programmer for review by the physician.

If the stability check succeeds on its initial try, the pacing threshold is likely to be below the amplitude of the delivered pacing pulses, indicating that a threshold test is more likely worthwhile. If the stability check fails on the first try at a given pacing amplitude, this may indicate to the physician that the pacing threshold at that location is likely undesirably high and that a complete threshold test may not be justified. An alternative implant location may then be tried.

Alternatively, if the retry of the stability check is successful, this may indicate that the likely pacing threshold is between the amplitudes of the pulses delivered during the first and second tries. If the amplitude of the pulses delivered during the re-try is acceptable, the physician may still go ahead with a threshold test at the present location.

Various examples of the disclosure have been described. These and other examples are within the scope of the following claims.

The invention claimed is:

1. A method for determining stability of a patient's intrinsic rhythm in a cardiac pacing device, comprising:
    delivering cardiac pacing pulses to a chamber of a patient's heart at a first pulse amplitude in a demand pacing mode;
    measuring a first series of intervals between successive events of the chamber, including sensed and paced events;
    determining whether the first measured series of intervals meets a stability criterion;
    responsive to the first measured series of intervals failing to meet the stability criterion, determining whether the first measured series of intervals includes an interval between a delivered pacing pulse and a sensed event that is less than a defined duration;
    responsive to the interval between a delivered pacing pulse and a sensed event being less than the defined duration, delivering cardiac pacing pulses to the chamber of a patient's heart at a second pulse amplitude in a demand pacing mode; and
    measuring a second series of intervals between successive events of the chamber, including sensed and paced events;
    determining whether the second measured series of intervals meets the stability criterion.

2. A method for determining stability of a patient's intrinsic rhythm in a cardiac pacing device, comprising:
    delivering cardiac pacing pulses to a chamber of a patient's heart at a first pulse amplitude in a demand pacing mode;
    measuring a first series of intervals between successive events of the chamber, including sensed and paced events;
    determining whether the first measured series of intervals meets a stability criterion;
    responsive to the first measured series of intervals failing to meet the stability criterion, determining whether the first measured series of intervals includes an interval between a delivered pacing pulse and a sensed event that is less than a defined duration;
    responsive to the interval between a delivered pacing pulse and a sensed event being less than the defined duration, delivering cardiac pacing pulses to the chamber of a patient's heart at a second pulse amplitude in a demand pacing mode; and
    measuring a second series of intervals between successive events of the chamber, including sensed and paced events;
    determining whether the second measured series of intervals meets the stability criterion; and
    wherein the pacing device defines refractory periods during which sensed events may occur, but wherein sensed events during the refractory periods are not considered in the measuring of the first series of intervals.

3. A method according to claim 1 wherein the pacing device defines refractory periods during which sensed events may occur, but wherein sensed events during the refractory periods are considered in the measuring of the first series of intervals.

4. A method according to claim 1, wherein prior to delivering pacing pulses at the second amplitude, the device determines whether the first amplitude is less than a defined amplitude and wherein delivery of pacing pulses at the second amplitude is performed responsive to the first amplitude being less than the defined amplitude.

5. A method according to claim 1 wherein responsive to either the first or second measured series of intervals meeting the stability criterion, the device performs a capture management operation.

6. A method according to claim 5 wherein the capture management operation includes one of a safety margin check or a threshold measurement test.

7. A cardiac pacing device, comprising:
    means for delivering cardiac pacing pulses to a chamber of a patient's heart at a first pulse amplitude in a demand pacing mode;
    means for measuring a first series of intervals between successive events of the chamber, including sensed and paced events;
    means for determining whether the first measured series of intervals meets a stability criterion;
    means responsive to the first measured series of intervals failing to meet the stability criterion, for determining whether the first measured series of intervals includes an interval between a delivered pacing pulse and a sensed event that is less than a defined duration;

means responsive to the interval between a delivered pacing pulse and a sensed event being less than the defined duration, for delivering cardiac pacing pulses to the chamber of a patient's heart at a second pulse amplitude in a demand pacing mode;

means for measuring a second series of intervals between successive events of the chamber, including sensed and paced events;

means for determining whether the second measured series of intervals meets the stability criterion.

8. A cardiac pacemaker, comprising:

means for delivering cardiac pacing pulses to a chamber of a patient's heart at a first pulse amplitude in a demand pacing mode;

means for measuring a first series of intervals between successive events of the chamber, including sensed and paced events;

means for determining whether the first measured series of intervals meets a stability criterion;

means responsive to the first measured series of intervals failing to meet the stability criterion, for determining whether the first measured series of intervals includes an interval between a delivered pacing pulse and a sensed event that is less than a defined duration;

means responsive to the interval between a delivered pacing pulse and a sensed event being less than the defined duration, for delivering cardiac pacing pulses to the chamber of a patient's heart at a second pulse amplitude in a demand pacing mode;

means for measuring a second series of intervals between successive events of the chamber, including sensed and paced events;

means for determining whether the second measured series of intervals meets the stability criterion; and wherein the pacemaker comprises means for defining refractory periods during which sensed events may occur, but wherein sensed events during the refractory periods are not considered in the measuring of the first series of intervals.

9. A pacing device according to claim 7 wherein the pacing device comprises means for defining refractory periods during which sensed events may occur, but wherein sensed events during the refractory periods are considered in the measuring of the first series of intervals.

10. A pacing device according to claim 7, comprising means for determining prior to delivering pacing pulses at the second amplitude, whether the first amplitude is less than a defined amplitude and for delivering pacing pulses at the second amplitude responsive to the first amplitude being less than the defined amplitude.

11. A pacing device according to claim 7 comprising means for performing a capture management operation responsive to either the first or second measured series of intervals meeting the stability criterion.

12. A pacing device according to claim 11 wherein the capture management operation includes one of a safety margin check or a threshold measurement test.

13. A non-transitory medium comprising instructions for determining stability of a patient's intrinsic rhythm in a cardiac pacing device, comprising instructions for:

delivering cardiac pacing pulses to a chamber of a patient's heart at a first pulse amplitude in a demand pacing mode;

measuring a first series of intervals between successive events of the chamber, including sensed and paced events;

determining whether the first measured series of intervals meets a stability criterion;

responsive to the first measured series of intervals failing to meet the stability criterion, determining whether the first measured series of intervals includes an interval between a delivered pacing pulse and a sensed event that is less than a defined duration;

responsive to the interval between a delivered pacing pulse and a sensed event being less than the defined duration, delivering cardiac pacing pulses to the chamber of a patient's heart at a second pulse amplitude in a demand pacing mode; and measuring a second series of intervals between successive events of the chamber, including sensed and paced events;

determining whether the second measured series of intervals meets the stability criterion.

14. A non-transitory medium comprising instructions for determining stability of a patient's intrinsic rhythm in a cardiac pacing device, comprising instructions for:

delivering cardiac pacing pulses to a chamber of a patient's heart at a first pulse amplitude in a demand pacing mode;

measuring a first series of intervals between successive events of the chamber, including sensed and paced events;

determining whether the first measured series of intervals meets a stability criterion;

responsive to the first measured series of intervals failing to meet the stability criterion, determining whether the first measured series of intervals includes an interval between a delivered pacing pulse and a sensed event that is less than a defined duration;

responsive to the interval between a delivered pacing pulse and a sensed event being less than the defined duration, delivering cardiac pacing pulses to the chamber of a patient's heart at a second pulse amplitude in a demand pacing mode; and measuring a second series of intervals between successive events of the chamber, including sensed and paced events;

determining whether the second measured series of intervals meets the stability criterion; and wherein the pacing device defines refractory periods during which sensed events may occur, but wherein sensed events during the refractory periods are not considered in the measuring of the first series of intervals.

15. A medium according to claim 13 wherein the pacing device defines refractory periods during which sensed events may occur, but wherein sensed events during the refractory periods are considered in the measuring of the first series of intervals.

16. A medium according to claim 13, comprising instructions for, prior to delivering pacing pulses at the second amplitude, determining whether the first amplitude is less than a defined amplitude and for performing delivery of pacing pulses at the second amplitude responsive to the first amplitude being less than the defined amplitude.

17. A medium according to claim 13 comprising instructions for performing a capture management operation responsive to either the first or second measured series of intervals meeting the stability criterion.

18. A medium according to claim 17 wherein the capture management operation includes one of a safety margin check or a threshold measurement test.

19. A method according to claim 1 wherein the first series of intervals includes pace to sensed depolarization, sensed depolarization to pace, pace to pace and sensed depolarization to sensed depolarization intervals.

20. A method according to claim 19 wherein the pacing device defines refractory periods during which sensed events may occur, but wherein sensed events during the refractory periods are not considered in the measuring of the first series of intervals.

21. A method according to claim 19 wherein the pacing device defines refractory periods during which sensed events may occur, but wherein sensed events during the refractory periods are considered in the measuring of the first series of intervals.

22. A pacing device according to claim 7 wherein the first series of intervals includes pace to sensed depolarization, sensed depolarization to pace, pace to pace and sensed depolarization to sensed depolarization intervals.

23. A pacing device according to claim 22 wherein the pacing device defines refractory periods during which sensed events may occur, but wherein sensed events during the refractory periods are not considered in the measuring of the first series of intervals.

24. A pacing device according to claim 22 wherein the pacing device defines refractory periods during which sensed events may occur, but wherein sensed events during the refractory periods are considered in the measuring of the first series of intervals.

25. A medium according to claim 13 wherein the first series of intervals includes pace to sensed depolarization, sensed depolarization to pace, pace to pace
and sensed depolarization to sensed depolarization intervals
and sensed depolarization to sensed depolarization intervals.

26. A medium according to claim 25 wherein the pacing device defines refractory periods during which sensed events may occur, but wherein sensed events during the refractory periods are not considered in the measuring of the first series of intervals.

27. A medium according to claim 22 wherein the pacing device defines refractory periods during which sensed events may occur, but wherein sensed events during the refractory periods are considered in the measuring of the first series of intervals.

* * * * *